United States Patent [19]
Hektner

[11] Patent Number: 6,050,986
[45] Date of Patent: Apr. 18, 2000

[54] CATHETER SYSTEM FOR THE DELIVERY OF A LOW VOLUME LIQUID BOLUS

[75] Inventor: Thomas R. Hektner, Medina, Minn.

[73] Assignee: SciMed Life Systems, Inc., Maple Grove, Minn.

[21] Appl. No.: 08/982,220

[22] Filed: Dec. 1, 1997

[51] Int. Cl.[7] .................................................. A61M 31/00
[52] U.S. Cl. ........................ 604/508; 604/264; 606/213
[58] Field of Search ........................ 604/500, 506–508, 604/510, 514–517, 264, 523, 15, 57, 59, 60, 181; 606/213, 214

[56] References Cited

U.S. PATENT DOCUMENTS

| | | | |
|---|---|---|---|
| 5,306,246 | 4/1994 | Sahatjian et al. | 604/96 |
| 5,702,384 | 12/1997 | Umeyama et al. | 603/892.1 |
| 5,746,728 | 5/1998 | Py | 604/298 |
| 5,820,610 | 10/1998 | Baudino | 604/280 |

FOREIGN PATENT DOCUMENTS

| | | |
|---|---|---|
| 0 202 658 | 4/1989 | European Pat. Off. . |
| WO 98/10824 | 3/1998 | WIPO . |

*Primary Examiner*—Corrine M. McDermott
*Attorney, Agent, or Firm*—Westman, Champlin & Kelly, P.A.

[57] ABSTRACT

A catheter system includes a catheter having a proximal end, a distal end, and a lumen extending therein. An elongate member slidably disposed in the lumen has a distal end located proximate the distal end of the catheter. An administering tip is disposed at the distal end of the catheter and is configured to express a bolus of liquid in response to positive pressure in a distal portion of the lumen created by movement of the elongate member distally in the lumen. The present invention also includes a method of administering a liquid to a treatment site. The distal end of the catheter is transluminally positioned proximate the treatment site. The catheter is charged by placing a bolus of the liquid in a distal end of the lumen between a distal tip of the catheter and a distal end of the elongate member. The elongate member is then moved distally within the lumen to express the bolus from the distal end of the catheter.

14 Claims, 4 Drawing Sheets

CATHETER SYSTEM FOR THE DELIVERY OF A LOW VOLUME LIQUID BOLUS

INCORPORATION BY REFERENCE

Reference is made to the following co-pending patent applications which are hereby fully incorporated by reference:

U.S. patent application Ser. No. 08/308,025, filed on Sep. 16, 1994, entitled "BALLOON CATHETER WITH IMPROVED PRESSURE SOURCE", which issued as U.S. Pat. No. 5,545,133 on Mar. 17, 1998.

U.S. patent application Ser. No. 08/586,514, filed Jan. 16, 1996, entitled "BALLOON CATHETER WITH IMPROVED PRESSURE SOURCE", which issued as U.S. Pat. No. 5,695,468 on Dec. 9, 1997.

U.S. patent application Ser. No. 08/319,375, filed May 21, 1996, entitled "BALLOON CATHETER WITH IMPROVED PRESSURE SOURCE", which issued as U.S. Pat. No. 5,728,064 on Mar. 17, 1998.

U.S. patent application Ser. No. 08/812,390, filed Mar. 5, 1997, entitled "BALLOON CATHETER WITH IMPROVED PRESSURE SOURCE", which issued as U.S. Pat. No. 5,785,685 on Jul. 28, 1998.

All of the above-referenced patent applications are assigned to the same assignee as the present application.

BACKGROUND OF THE INVENTION

The present invention deals with catheters. More specifically, the present invention deals with delivery of a small bolus of liquid with a catheter.

A wide variety of different mechanisms and techniques have been developed in order to treat coronary disease. However, such techniques and devices are typically drawn to the physical manipulation of biological tissues, such as heart tissue, or other vascular tissue within the vascular system.

For example, some treatment techniques are drawn to the physical removal or dilation of restrictions (stenoses and total occlusions) in the vasculature. Techniques for dealing with this type of disease have included percutaneous transluminal coronary angioplasty (PTCA) in which an angioplasty balloon catheter is inserted into the body via the femoral artery and positioned across a restriction in an artery. The balloon is inflated to widen the restriction and restore blood flow to portions of the heart muscle previously deprived of oxygenated blood. Implantation of stents using PTCA is also a common technique for opening an arterial restriction.

Another technique for dealing with vascular disease includes coronary artery bypass graft (CABG) procedures. Such procedures typically include the placement of a graft at a desired location in the vasculature to supplement blood flow to the area previously deprived of blood for (or provided with reduced blood flow) due to the vascular restriction. One common type of CABG procedure involves placement of a sapphenous vein graft (SVG) between the ascending aorta proximal of the restriction, and a region in the restricted vessel distal of the restriction.

Another technique for dealing with vascular disease includes an atherectomy procedure. In an atherectomy procedure, an atherectomy device is placed in the vasculature proximate the restriction. The atherectomy device is deployed to physically cut away, abrade, or otherwise physically remove, the occlusive material from the restricted vessel. The portions of the restriction which are severed by the atherectomy device are subsequently removed by aspiration, or by another suitable device.

Another technique called transluminal myocardial revascularization is also receiving attention in the medical community as an acceptable therapy.

Various drug therapies have also been developed. Such therapies have been used in place of, and in conjunction with, the above mentioned therapies under certain circumstances. For example, during grafting procedures, it may be desirable to deliver drugs to the graft site which inhibit the formation of thrombus. In addition, some drug therapies have been developed which involve the delivery of drugs directly to the heart tissue. With recent advancements in the pharmaceutical industry, other drug therapies have also become desirable. Some such recent pharmaceutical developments include the development of gene therapy drugs, such as growth factors.

A transluminal technique for delivering the drugs, along with the various types of known positioning and visualization techniques commonly used with transluminal treatments, can be highly desirable. The drug therapies typically require site specific administration of the drug. Transluminal techniques can be effectively used to deliver a liquid material to a selected site in the vasculature.

However, drug therapies, can be prohibitively expensive. For example, newly developed drugs are commonly extremely expensive and can only be administered in any pragmatic fashion in very low volumes. Typically, such drugs only need to be administered to the vascular site being treated. However, there is no technique available to date by which the site to be treated can be accessed transluminally with a catheter and which enables only a very small quantity of drug to be delivered from the distal tip of the catheter to the treatment site.

Rather, conventional transluminal drug delivery catheters require a proximal infusion device which is connected to a proximal end of the infusion catheter and which is used to pressurize a fluid or infusate which contains the drug to be delivered. The catheter is filled with the infusate and the drug is administered at the distal tip of the infusion catheter (upon pressurization of the infusate) after the catheter is inserted and properly positioned. While the internal volume of such infusion catheters is typically small, it is still much too large to make drug delivery with extremely expensive drugs practical.

SUMMARY OF THE INVENTION

The present invention is drawn to the delivery of a low volume bolus of drug or other treatment material to the myocardium, a vessel, or any other organ or area for which transluminal access is desirable. For example, anti-arrhythmia drugs may be injected into the myocardium using the present invention for electrophysiological therapy. Also, growth factors and other gene therapy substances can be injected into the myocardium for myocardial revascularization.

The catheter system includes a catheter having a proximal end, a distal end, and a lumen extending therein. An elongate member slidably disposed in the lumen has a distal end located proximate the distal end of the catheter. An administering tip is disposed at the distal end of the catheter and is configured to express a bolus of liquid in response to positive pressure in a distal portion of the lumen created by movement of the elongate member distally in the lumen.

The present invention also includes a method of administering a liquid to a treatment site. A catheter, having a proximal end, a distal end and a lumen extending therein, as well as an elongate member, slidably disposed in the lumen, are provided. The distal end of the catheter is transluminally positioned proximate the treatment site. The catheter is charged by placing a bolus of the liquid in a distal end of the lumen between a distal tip of the catheter and a distal end of the elongate member. The elongate member is then moved distally within the lumen to express the bolus from the distal end of the catheter.

Also, the present device should not be limited to implementation using only conventional catheters per se, but also contemplates any steerably, maneuverable syringe structure. Thus, the term catheter should be construed to include both conventional catheters and elongate, maneuverable syringe barrel structures suitable for maneuvering, manipulation, tracking and steering within a vessel.

The catheter system can be navigated through several lumens and cavities within the body. Intravascular access by the femoral, brachial and radial arteries is contemplated for accessing target sites within the heart or peripheral vasculature. Alternatively, the catheter may be navigated into the ventricles of the heart by way of the aorta for direct treatment of the heart muscle (myocardium). Yet another alternative for accessing the heart chamber is via the vena cava. Lastly, nonvascular ducts or lumens within the body can be accessed for drug delivery such as for cancer treatment.

DETAILED DESCRIPTION OF THE PREFERRED EMBODIMENTS

Figure 1:
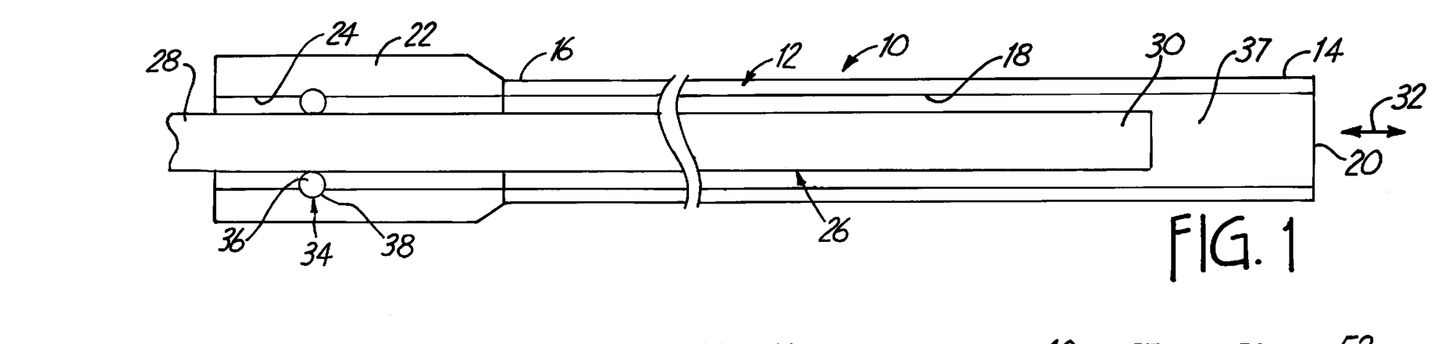
FIG. 1 is a side sectional view of a catheter system in accordance with one preferred embodiment of the present invention.

FIG. 1 is a side sectional view of a catheter system 10 in accordance with one preferred embodiment of the present invention. Catheter system 10 includes catheter 12 having a distal end 14 and a proximal end 16 and a lumen 18 running therethrough. In the embodiment shown in FIG. 1, distal end 14 is simply an open end providing distal opening 20, and proximal end 16 is coupled to proximal manifold 22 in any known conventional manner.

Manifold 22 preferably has a lumen 24 extending therethrough which is coaxial with lumen 18. Lumen 24 is also preferably in fluid communication with lumen 18.

System 10 also preferably includes piston rod 26. Piston rod 26 is preferably an elongate member which extends from a proximal end 28 (which preferably extends to a region proximal of manifold 22) to a distal end 30 which is preferably proximate distal end 14 of catheter 12. Piston rod 26 preferably has an outer diameter which is just smaller than the inner diameter of lumen 18. Also, piston rod 26 is preferably slidably disposed within lumen 18 such that piston rod 26 can slide in a direction generally parallel to the longitudinal axis of catheter 18, in the direction indicated by arrow 32.

Piston rod 26 is supported for reciprocal movement within lumen 18 by virtue of its outer dimensions relative to the inner dimensions of lumen 18, and also be seal arrangement 34. Seal arrangement 34 is preferably an o-ring type seal which fluidically seals the interior of lumen 18 from the exterior of system 10 through the proximal end of manifold 22. Thus, seal arrangement 34 preferably includes an o-ring 36 which is disposed within a generally annular depression or recess 38 formed in lumen 24 of manifold 22. O-ring 36 is preferably formed of a conventional sealing material, such as silicon rubber, and is secured in annular recess 38 utilizing a suitable adhesive.

The distal end 30 of rod 26, when positioned as shown in FIG. 1, preferably cooperates with the inner periphery of the distal end 14 of catheter 12 to form a bolus chamber 37 for containing a bolus of treatment material. The treatment material contained in chamber 37 can be a drug, growth factors, gene therapy materials, radioactive fluid for restenosis or cancer treatment, clot dissolution agent, or any other desired fluid or liquid material. Also, the material can be injected by high pressure, at high velocity, to mechanically break up clots. As described later in the specification, material delivered by system 10 is administered to a desired site in the body by reciprocation of rod 26 in lumen 18.

The proximal end 28 of piston rod 26 is preferably formed in any suitable manner which allows the user to easily grasp and reciprocate rod 26 within lumen 18. For example, in the above-identified patent applications which are hereby fully incorporated by reference, a number of different proximal grasping and manipulating members are disclosed. In one arrangement, a threadable connection is provided between proximal end 28 of rod 26 and manifold 22. In this way, the user can rotate rod 26 to cause either proximal or distal reciprocal movement within lumen 18. In another preferred embodiment, a release mechanism is provided such that the threadable engagement between rod 26 and manifold 22 can be disengaged to simply push or pull rod 26 for quicker longitudinal movement of rod 26. Then, for finer adjustment of rod 26, the threaded engagement is re-engaged and rod 26 is rotated to accomplish longitudinal movement. Further, in the references which are incorporated herein, various grasping members are provided to facilitate grasping and manipulation of rod 26 by the user. Also, electromechanical (e.g., solenoid) actuation of rod 26 can also be used.

In any case, in a preferred embodiment, catheter 12 is preferably formed of a suitable material to track through desired vasculature and to access a treatment site in the body. Therefore, in operation, prior to being inserted in the vasculature, catheter 12 is preferably filled with a solution, such as saline, such that all areas between rod 26 and the inner wall of lumen 18 are filled with the liquid solution to eliminate any dead space in lumen 18. A therapeutic drug or other fluid material is then loaded into the distal end 14 of catheter 18. This may be done, for example, by moving rod 26 to a position in which its distal end 30 is approximately co-terminus with the opening 20 in lumen 18 of catheter 12. Then, distal end 14 of catheter 12 is placed in the liquid solution to be introduced into the vasculature, and rod 26 is withdrawn a desired distance proximally. Withdrawing rod 26 proximally creates a vacuum in chamber 37 of catheter 12 and thus draws some of the liquid solution to be introduced into chamber 37 of catheter 12. In one preferred embodiment, visual indicia are provided at the proximal end 28 of rod 26 to indicate to the user the total volume of liquid solution which has been drawn into the distal end 14 of catheter 12 based on proximal withdrawal of rod 26.

After catheter 12 has been charged with the treatment solution, distal end 14 of catheter 12 is advanced through the vasculature and positioned proximate a desired treatment site. This can be accomplished in any number of known manners. For example, the distal tip 14 of catheter 12 can be provided as a cutting tip which can be used to pierce the skin and enter the desired vessel. Further, a separate cutting device can be provided which is used in conjunction with (e.g., over the top of) catheter 12 to introduce catheter 12 into the desired vessel. Still further, conventional guidewire or guide catheter assemblies can be used in conjunction with catheter 12 to guide catheter 12 to a desired location in the vasculature. Use of a guidewire with catheter 12 is preferably accomplished by either providing a separate lumen in catheter 12, separate from lumen 18, over which catheter 12 can track the guidewire. Alternatively, catheter 12 can be formed as a single-operator-exchange catheter which includes a distal guidewire tube for tracking over the guidewire. Such arrangements are more fully discussed in the above-referenced U.S. patent applications.

In any case, distal end 14 of catheter 12 is advanced under suitable visualization, or according to other positioning techniques, until it resides proximate the site to be treated. Once appropriately positioned, the user advances rod 26 distally such that the distal end 30 of rod 26 creates a positive pressure within chamber 37 of lumen 18 at the distal end 14 of catheter 12. This positive pressure forces the liquid treatment material out the distal opening 20 in catheter 12 so that it is administered at the desired.

In a preferred embodiment, the volume of the chamber 37, which is defined by the interior periphery of catheter 12 and the distal tip of rod 26, is preferably less than or equal to approximately 1 ml. Thus, it can be seen that the present invention can be used to directly administer a very low volume bolus of drug or other therapeutic material directly to a desired treatment site within the body, using a transluminal technique.

The specific materials used in implementing catheter system 10 can be any suitable, and commercially available materials. For example, manifold 22 is preferably made of an injection molded polycarbonate. Recess 38 within which o-ring 36 resides preferably has approximately a 0.123 inch diameter recess formed in manifold 22, and the inner diameter of lumen 24 in manifold 22 is preferably approximately 0.042 inches. Catheter 12 can be formed of several sections, or only a single section. Catheter 12 can also be made of any suitable materials, depending on the performance characteristics desired. For example, catheter 12 can be made of an extruded polymer tube, stainless steel hypotube, or a composite material such as stainless steel braid encased in polyimide. To impart different characteristics along its length, catheter 12 may incorporate changes in diameter or combine different constructions. For example, catheter 12 may have a composite proximal section combined with a polymer distal section. Other suitable configurations can be used as well.

Rod 26 is preferably made of a stainless steel wire surrounded by a Kynar™ tube. The stainless steel wire preferably has a diameter of approximately 0.019 inches and a length of about 50 inches. The tube surrounding the wire preferably has an outside diameter of approximately 0.038 inches and an inside diameter of 0.020 inches. When fully actuated in the distal direction, rod 26 preferably extends such that its distal end 30 is co-terminus with the distal end 14 in catheter 12. Positive stops (not shown) can optionally be provided at the distal end 14 of catheter 12 to limit the distal movement of rod 26.

Generally, connections between the various polymer components may be made utilizing suitable grade medical adhesives or thermal bonds which are well known to those skilled in the art. Connections between metallic components are preferably made, for example, by utilizing solder, by brazing, welding, or other suitable techniques.

Figure 2:
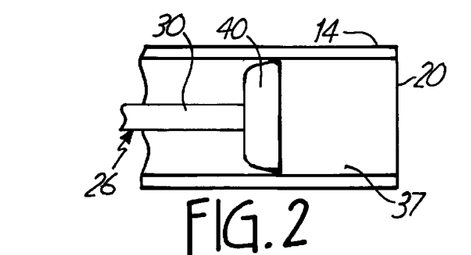
FIG. 2 is an enlarged side sectional view of a second embodiment of a distal tip of the catheter system in accordance with the present invention.

FIG. 2 is an enlarged view of a distal end portion 14 of catheter 12. Some items shown in FIG. 2 are similar to those shown in FIG. 1, and are correspondingly numbered. However, FIG. 2 illustrates that, rather than rod 26 simply having distal end 30, a plunger 40 is coupled to distal end 30 of rod 26. Plunger 40 has an outer diameter which is approximately the same as, or just smaller than, the inner diameter of lumen 18. Thus, when rod 26 is actuated in the distal direction, plunger 40 and rod 26 act much like a conventional syringe in that the distal chamber 37 defined by the distal end 14 of catheter 12 and plunger 40, is pressurized. This forces the bolus of treatment material out through the distal opening 20 in catheter 12. However, since plunger 40 is provided, the outer periphery of the remainder of actuating rod 26 need not be approximately the same as, or just smaller than, the interior periphery of lumen 18. Instead, it can be much smaller. This significantly reduces the frictional forces acting on rod 26 as it is reciprocated within lumen 18. It should be noted that plunger 40 can be a separate member attached to the distal end 30 of rod 26, or it can be formed integrally with rod 26 simply by broadening out the distal end 30 of rod 26.

Figure 3:
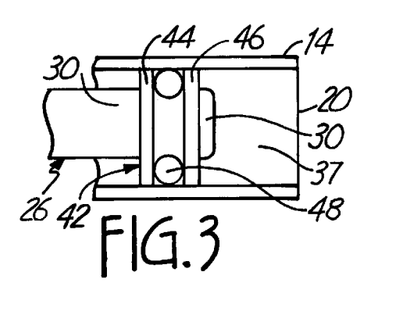
FIG. 3 is an enlarged view of the distal end of a catheter system in accordance with another preferred embodiment of the present invention.

FIG. 3 is another enlarged view of the distal end of rod 26. Some items are similar to those shown in FIG. 2, and are similarly numbered. However, rather than having simply plunger 40, the embodiment shown in FIG. 3 includes plunger head 42. Plunger head 42 includes a pair of discs 44 and 46 which are mounted about the outer periphery of the distal end 30 of rod 26. The discs 44 and 46 are preferably separated by an o-ring 48 formed of silicone or other suitable material and sized to fluidically seal lumen 18. Discs 44 and 46 are also preferably formed of silicon rubber material, or other suitable material, or can be formed integrally with rod 26.

Figure 4:
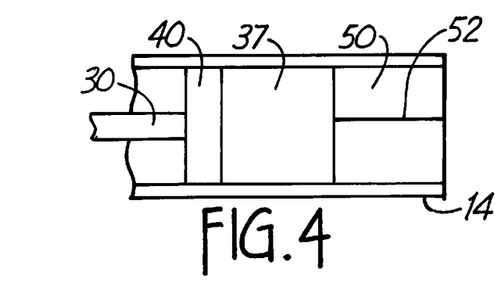
FIG. 4 is an enlarged side sectional view of another embodiment of a distal tip of the catheter system in accordance with the present invention.

FIG. 4 is an enlarged side sectional view of the distal end 14 of catheter 12 in accordance with another aspect of the present invention. Some items are similar to those shown in FIG. 2 and are correspondingly numbered. However, rather than simply having a distal opening 20 in the distal end 14 of catheter 12, FIG. 4 illustrates that a separable seal 50 is provided in distal end 14. Separable seal 50 preferably includes a rubber or polymer material inserted into the distal end 14 of catheter 12 and connected thereto with a suitable adhesive.

Separable seal 50 preferably includes a seam 52 therein. Seam 52 is simply formed by the abutment of the surfaces of seal 50 against one another, but those portions are not adhesively or otherwise sealed to one another (other than through friction). This arrangement allows the introduction of a conventional, small diameter, needle which is attached to a syringe containing the treatment solution into the distal end 14 (and hence chamber 37) of catheter 12, and through seam 52. Thus, the treatment solution can be injected into chamber 37 of catheter 12, as plunger 40 is withdrawn in the proximal direction to draw the treatment solution therein.

Once the distal end 14 of catheter 12 is placed at the treatment site in the vasculature, distal actuation of rod 26 causes plunger 40 to create a pressure behind seal 50 causing seal 50 to separate at seam 52 and thus release the treatment solution at the desired location. In another preferred embodiment, seal 50 is a rolling diaphragm type of seal, or another suitable type of seal configuration.

Figure 5:
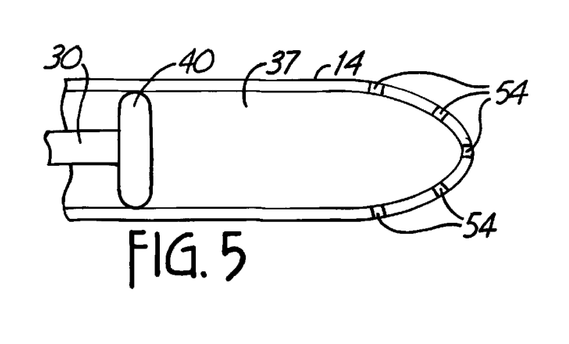
FIG. 5 is an enlarged side sectional view of another embodiment of a distal tip of the catheter system in accordance with the present invention.

FIG. 5 is an enlarged side sectional view of distal end 14 of catheter 12 in accordance with another aspect of the present invention. Similar items are similarly numbered to those shown in previous figures. However, FIG. 5 illustrates that the distal tip of catheter 12 is provided with a needle having a plurality of apertures 54 therein. Apertures 54 allow the treatment solution 37 to be withdrawn into the distal end 14 of catheter 12, and to be forced out through the distal end thereof.

Figure 6:
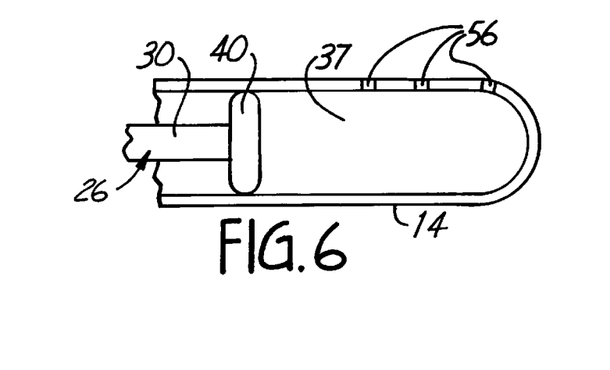
FIG. 6 is an enlarged side sectional view of another embodiment of a distal tip of the catheter system in accordance with the present invention.

FIG. 6 illustrates yet another embodiment in accordance with the present invention. FIG. 6 is similar to FIG. 5 except that, rather than having uniformly spaced apertures 54 at the distal tip of catheter 12, the distal tip or nozzle region is provided with side ports 56 which allow the treatment solution in chamber 37 to be directionally administered in the direction in which side ports 56 are disposed.

Figure 7:
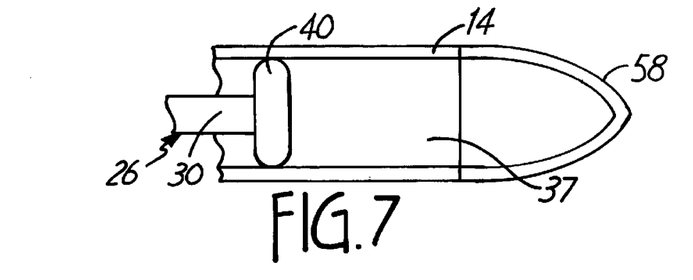
FIG. 7 is an enlarged side sectional view of another embodiment of a distal tip of the catheter system in accordance with the present invention.

FIG. 7 illustrates another preferred embodiment in accordance with the present invention. Similar items are similarly numbered to those shown in previous figures. However, the distal end of catheter 12, rather than being provided as a solid member with apertures therein, is provided as a porous needle portion 58. Porous needle portion 58 can be provided as a microporous membrane, as a selectively porous membrane, or as any other suitable porous or capillary type material, suitable for the introduction of treatment solution from chamber 37 to the treatment site.

Figures 8, 9:
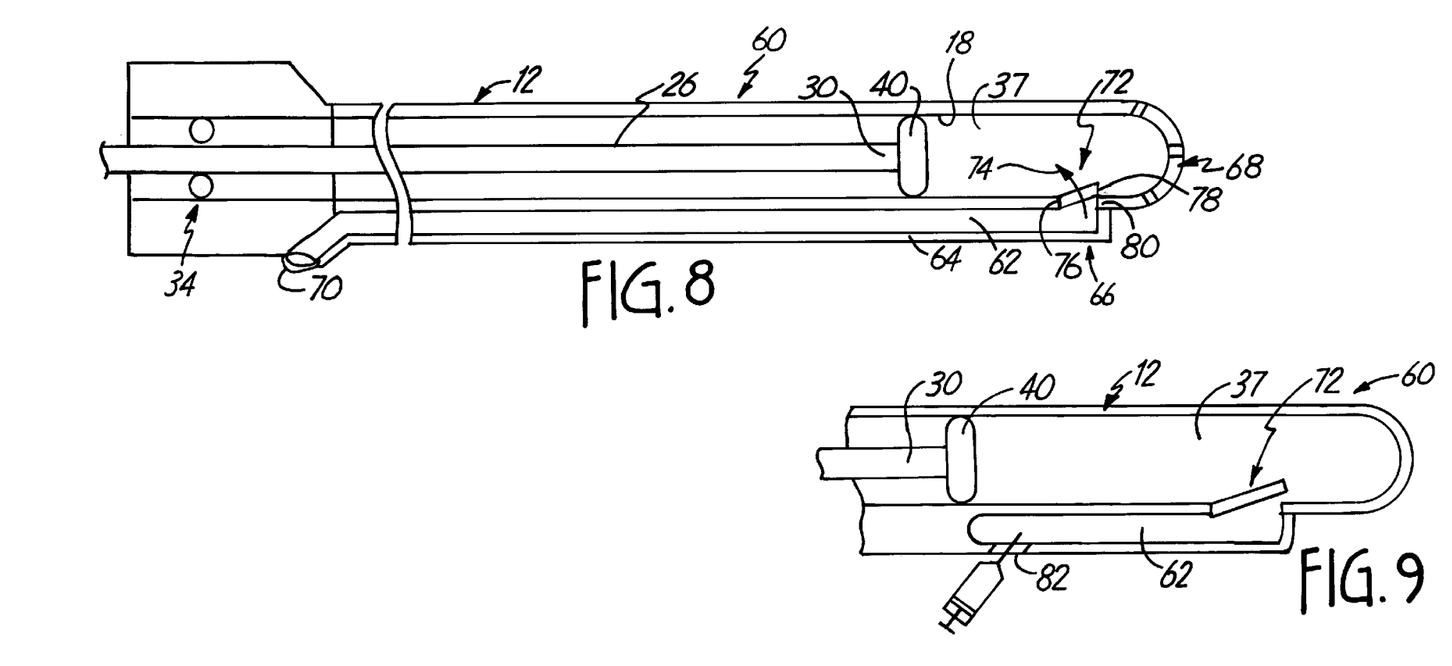
FIG. 8 is a side sectional view of another embodiment of a catheter system in accordance with the present invention.
FIG. 9 is a side sectional view of the catheter system of FIG. 8, with a modified liquid reservoir configuration.

FIG. 8 is a side sectional view of a catheter system 60 in accordance with another preferred embodiment of the present invention. Some items are similar to those shown in FIGS. 1–7, and are similarly numbered. However, catheter 12 is also provided with a treatment fluid reservoir 62 defined by wall 64 which is preferably arranged about an exterior portion of catheter 12. Reservoir 62 extends from a distal end 66 which is arranged just proximal of administration tip (or nozzle) 68, to a proximal end 70 which is provided with a suitable fitting for receiving the treatment solution.

In operation, the treatment solution is preferably injected, using a standard syringe, through proximal portion 70 of reservoir 62. A flapper valve 72 is preferably provided at distal end 66 of reservoir 62 to fluidically separate lumen 18 in catheter 12 from reservoir 62. In the preferred embodiment, flapper valve 72 is arranged such that it pivots generally in a direction indicated by arrow 74 and is hingedly attached by hinge 76 to the wall of catheter 12. Flapper valve 72 has a distal end 78 which engages a positive stop 80 on the inside of lumen 18 of catheter 12.

Therefore, when plunger 40 is withdrawn proximally, this creates a vacuum or low pressure area within chamber 37, relative to reservoir 62. This causes flapper valve 72 to lift upwardly to allow fluid to escape from reservoir 62 into chamber 37. Then, when plunger 40 is advanced distally, this creates a high pressure region in lumen 18 relative to reservoir 62 so that flapper valve 72 closes and the distal end 78 of flapper valve 72 abuts positive stop 80.

As plunger 40 continues to be advanced distally, the treatment solution in chamber 37 is passed through administering tip 68 to the desired site. In the preferred embodiment, administering tip 68 is provided with very small apertures, or pores, or valved openings, such that a greater pressure differential is required between the interior lumen 18 and the exterior of catheter 12 to cause liquid material to pass through administering tip 68 than is required to lift flapper valve 72. Therefore, as plunger 40 is withdrawn proximally, flapper valve 72 opens to allow the treatment material in chamber 62 to enter lumen 18, but no fluid, or very little fluid, is drawn into lumen 18 from outside catheter 12. Then, as plunger 40 is advanced distally, flapper valve 72 closes and a great enough pressure is built within chamber 37 to cause the treatment material to pass through administering tip 68 to the desired position.

It will thus be appreciated that the embodiment disclosed in FIG. 8 allows the user to position distal tip 14 of catheter 12 at the desired location within the body before chamber 37 is charged with the bolus of treatment material to be injected at the treatment site.

FIG. 9 shows another embodiment of the distal end 14 of catheter 12 in catheter system 60. Similar items are similarly numbered to those shown in FIG. 8. However, rather than providing reservoir 62 extending all the way from distal end 66 thereof to proximal end 70 thereof, reservoir 62 is maintained only at a distal portion of catheter 12. Reservoir 62 is also provided with a suitable introduction valve 82 which can preferably be used in conjunction with a conventional syringe, to introduce the bolus of treatment material into reservoir 62. By not requiring reservoir 62 to extend all the way to the proximal end 70, the internal volume of reservoir 62 can be kept very small. This facilitates utilizing only a needed volume of treatment material. No extra material is required to fill the internal volume of reservoir 62, since that volume is so small.

Figure 10:
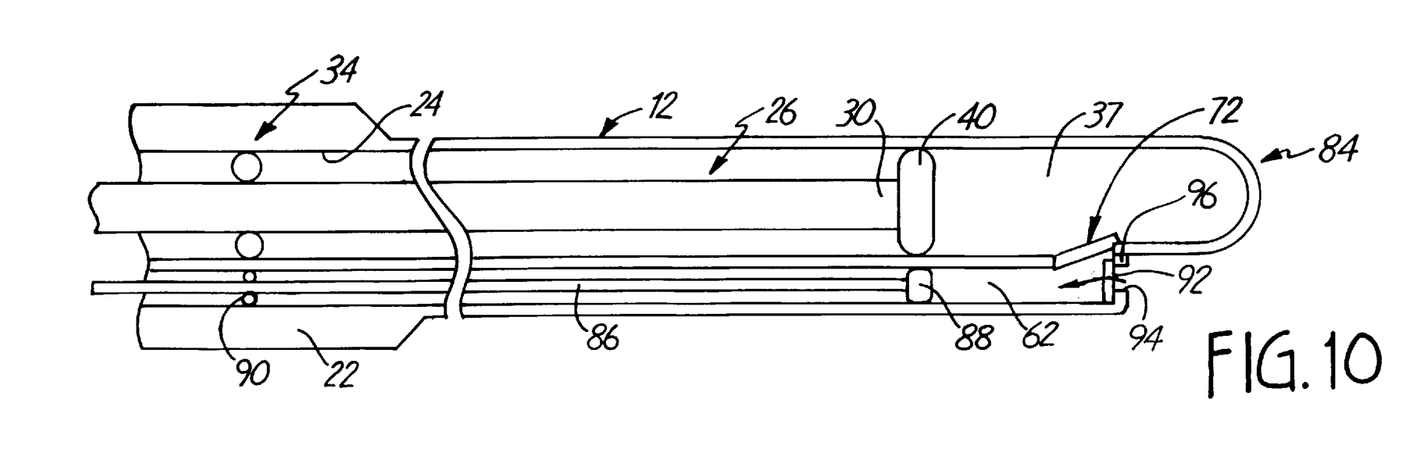
FIG. 10 is a side sectional view of a catheter system in accordance with one aspect of the present invention, deploying a two piston arrangement.

FIG. 10 shows another preferred embodiment of the catheter system 84 in accordance with the present invention. Catheter system 84 is similar to catheter system 60 shown in FIG. 8, and similar items are similarly numbered. However, catheter system 84 includes a modified form of treatment reservoir 62. Rather than terminating in its proximal area at proximal end 70, the proximal end of reservoir 62 in catheter system 84 extends all the way through proximal manifold 22 in the same fashion as lumen 24. Also, reservoir 62 is provided with a reciprocally mounted rod 86 and plunger 88. Further, rod 86 is sealably mounted within manifold 22 by seal configuration 90 which is similar to seal configuration 34 discussed with respect to FIG. 1. The proximal ends of rods 26 and 86 can optionally be either connected to one another, or separate from one another for separate actuation by the user.

In any case, in order to introduce the bolus of treatment material into reservoir 62, rod 86 and plunger 88 are advanced to the distal most actuation point in which they abut a second flapper valve arrangement 92. Flapper valve 92 is biased to normally close an aperture 94 against an inner portion 96 of the distal end of reservoir 62. Then, the distal tip 14 of catheter 12 and reservoir 62 are placed in the drug solution to be administered. Rod 86 and plunger 88 are then withdrawn distally a desired amount such that flapper valve 92 opens to allow the fluid to be administered to enter reservoir 62 through aperture 94. When the distal tip 14 of catheter 12 is appropriately positioned in the vasculature, rod 86 and plunger 88 are then advanced distally to charge catheter 12 by introducing the material to be administered from reservoir 62, through flapper valve arrangement 72, and into chamber 37 in catheter 12. Once charged, catheter 12 is ready to administer the treatment solution. Thus, the user advances rod 26 and plunger 40 such that the bolus of treatment solution is injected from chamber 37 through the administering tip of catheter 12 to the desired site.

Figure 11:
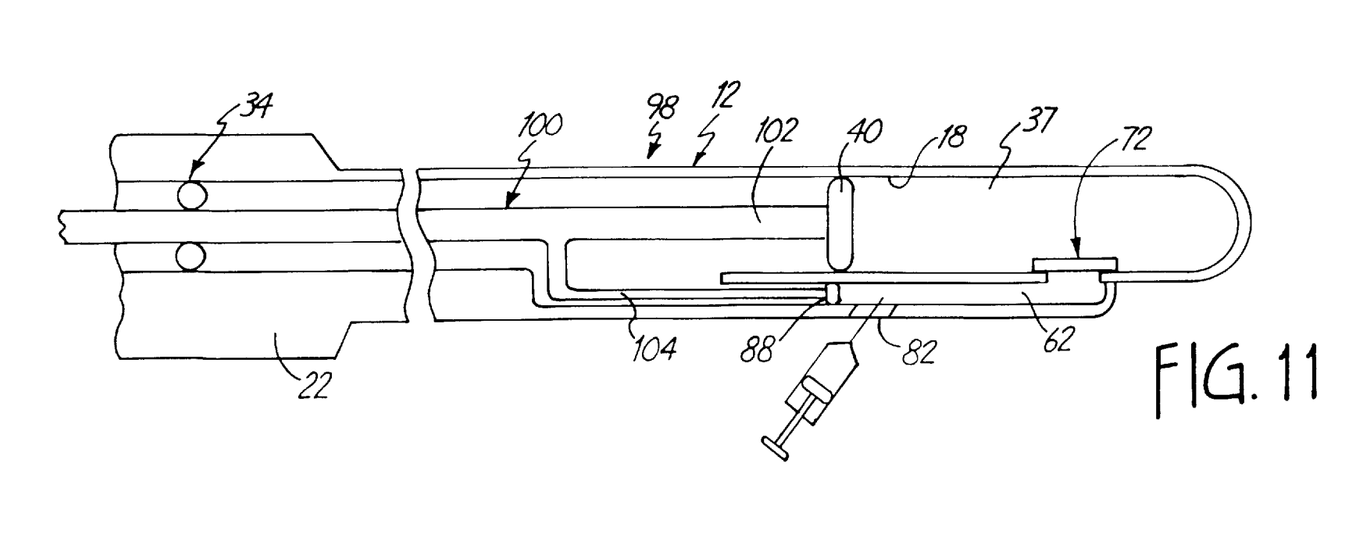
FIG. 11 is a side sectional view of a catheter system in accordance with one aspect of the present invention utilizing a bifurcated piston configuration.

FIG. 11 shows another catheter system 98 in accordance with another preferred embodiment of the present invention. Similar items are similarly numbered to those shown in previous figures. Catheter system 98 is similar to catheter system 84 and similar items are correspondingly numbered. However, rather than providing two rods 26 and 86, as in FIG. 10, catheter system 98 includes bifurcated rod 100. Bifurcated rod 100 includes first leg portion 102 which is connected to plunger 40 and which resides within lumen 18 of catheter 12. Bifurcated rod 100 also includes second leg portion 104 which is connected to plunger 88 and lies in reservoir 62. Catheter system 98 shown in FIG. 11 is also preferably provided with a valve arrangement similar to valve arrangement 82 shown in FIG. 9 by which the treatment material is inserted into reservoir 62.

In the embodiment shown in FIG. 11, the treatment material is simultaneously introduced from reservoir 62 into chamber 37 distal of plunger 40, and it the bolus of material is injected at the desired site, as the user advances bifurcated rod 100 distally. Plunger 88 causes high pressure in reservoir 62 to move the bolus of treatment material from reservoir 62 into chamber 37 distal of plunger 40. At the same time, plunger 40 causes high pressure to be developed in chamber 37 such that the bolus of material is advanced through the administering tip to the desired site.

Figure 12:
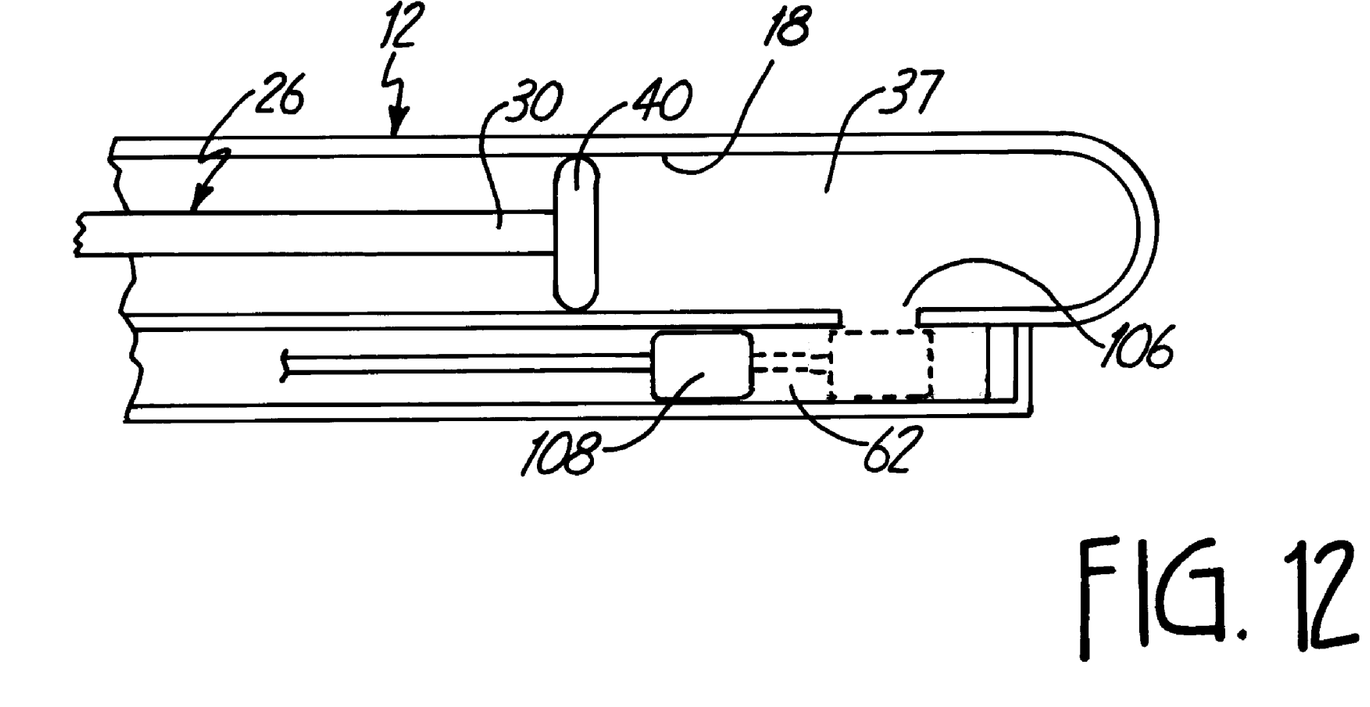
FIG. 12 is a side sectional view of a catheter system in accordance with one aspect of the present invention utilizing a valve and engageable valve seat configuration.

FIG. 12 is similar to FIGS. 10 and 11, and similar items are similarly numbered. However, reservoir 62 is provided with different valve arrangements. Rather than flapper valve 72, a simple aperture 106 is provided between reservoir 62 and lumen 18. A plunger 108 is sized to completely cover aperture 106 when it is advanced to its distal most position (shown in phantom in FIG. 12). Thus, the operator can advance plunger 108 within reservoir 62 to charge lumen 18 with a bolus of material. The operator can, either simultaneously or separately, advance plunger 40 to administer the material through the tip of the catheter, once chamber 37 has been charged with the bolus.

Thus, it can be seen that the present invention provides a number of advantages over prior art infusion techniques. The present invention can be utilized to transluminally access a site to be treated within the body. The present invention can also be utilized to administer a therapeutic solution, or any desired solution, at that site. Further, the present invention can be utilized to administer only a very small volume bolus of material, preferably less than 1 milliliter at the site. This allows the pragmatic administration of even very expensive drugs in an efficient and accurate manner.

It should also be noted, of course, that the distal tip of the catheter can be arranged to provide any sort of nozzle configuration. The distal tip can be valved, it can have apertures uniformly distributed thereabout, it can have apertures directionally distributed thereabout, and it can have apertures which provide desired injection or dispersion characteristics.

Although the present invention has been described with reference to preferred embodiments, workers skilled in the art will recognize that changes may be made in form and detail without departing from the spirit and scope of the invention.

What is claimed is:

1. A method of administering a liquid to a treatment site in a human body, the method comprising:

providing a catheter having a proximal end, a distal end, and a lumen extending therein;

providing an elongate member, slidably disposed in the lumen, and having a distal end located proximate the distal end of the catheter;

providing a bolus reservoir having an outlet fluidly coupleable to a distal portion of the catheter lumen for fluid communication with the lumen;

filling the bolus reservoir with fluid transluminally positioning the distal end of the catheter into a body lumen proximate the treatment site;

moving the elongate member proximally within the lumen;

creating a pressure differential between the distal end of the lumen and the reservoir to move the bolus into the distal end of the lumen from the reservoir to charge the catheter with a bolus of liquid between a distal tip of the catheter and the distal end of the elongate member; and sliding the elongate member distally within the lumen of the catheter disposed in the body lumen to express the bolus into the body lumen from the distal end of the catheter.

2. The method of claim 1 wherein providing a bolus reservoir comprises:

providing a valve at the outlet between the bolus reservoir and the distal end of the lumen, the valve being configured to move between an open position providing liquid communication between the reservoir and the lumen, and a closed position inhibiting liquid communication between the reservoir and the lumen.

3. The method of claim 1 wherein creating a pressure differential comprises:

providing a second elongate member slidably within the reservoir; and sliding the second elongate member distally within the reservoir to increase pressure in the reservoir relative to pressure in the lumen.

4. The method of claim 3 wherein the bolus reservoir includes a distal inlet having a normally closed valve and comprising the steps of:

inserting the distal inlet of the bolus reservoir into bolus; and retracting the second elongated member to open the normally closed valve to charge the bolus reservoir with bolus.

5. The method of claim 1 wherein providing a bolus reservoir comprises:

providing the reservoir as a shaft having a reservoir lumen extending from a distal portion of the catheter to a proximal portion of the catheter; and introducing the bolus into the reservoir lumen from a proximal end of the reservoir lumen.

6. A catheter system for delivering a bolus of liquid to a treatment site in a human body comprising:

a catheter having a proximal end, a distal end, and a lumen extending therein and formed of a material suitable for transluminally tracking through the vascular system to the treatment site, an extent of the catheter between the proximal and distal ends being profiled for transluminal advancement of the distal end of the catheter through a body lumen to a treatment site with the proximal end external to the body lumen for operation;

an elongate member, slidably disposed in the lumen, and having a distal end located proximate the distal end of the catheter, the lumen and elongate member forming a chamber defined by the distal end of the elongate member and an inner periphery of the distal end of the catheter, the chamber being configured to receive the bolus;

an administering tip disposed at the distal end of the catheter, configured to express the bolus of liquid in response to positive pressure in a distal portion of the lumen created by movement of the elongate member distally in the lumen;

a wall defining a reservoir having a distal portion located proximate the chamber and being configured to provide liquid communication between the reservoir and the chamber, the reservoir including an aperture in liquid communication with the chamber; and a liquid retainer covering the aperture, the retainer retaining the bolus in the reservoir and being configurable to enable movement of the bolus from the reservoir to the chamber.

7. The catheter system of claim 6 wherein the liquid retainer comprises:

a pressure responsive valve coupled to the outlet moveable between an opened position for liquid communication between the reservoir and the chamber and a closed position in response to a pressure differential across the pressure responsive valve.

8. A catheter system for delivering a bolus of liquid to a treatment site in a human body comprising:

a catheter having a proximal end, a distal end, and a lumen extending therein and formed of a material suitable for transluminally tracking through the vascular system to the treatment site, an extent of the catheter between the proximal and distal ends being profiled for transluminal advancement of the distal end of the catheter through a body lumen to a treatment site with the proximal end external to the body lumen for operation;

an elongate member, slidably disposed in the lumen, and having a distal end located proximate the distal end of the catheter, the lumen and elongate member forming a chamber defined by the distal end of the elongate member and an inner periphery of the distal end of the catheter;

an administering tip disposed at the distal end of the catheter, configured to express the bolus of liquid in response to positive pressure in a distal portion of the lumen created by movement of the elongate member distally in the lumen; and a wall defining a reservoir located proximate the chamber and being configured to provide liquid communication between the reservoir and the chamber and the reservoir is located substantially entirely proximate the distal end of the catheter.

9. The catheter system of claim 8 wherein the reservoir includes a valve configured to receive the bolus by injection from a syringe.

10. A catheter system for delivering a bolus of liquid to a treatment site in a human body comprising:

a catheter having a proximal end, a distal end, and a lumen extending therein and formed of a material suitable for transluminally tracking through the vascular system to the treatment site, an extent of the catheter between the proximal and distal ends being profiled for transluminal advancement of the distal end of the catheter through a body lumen to a treatment site with the proximal end external to the body lumen for operation;

an elongate member, slidably disposed in the lumen, and having a distal end located proximate the distal end of the catheter, the lumen and elongate member forming a chamber defined by the distal end of the elongate member and an inner periphery of the distal end of the catheter;

an administering tip disposed at the distal end of the catheter, configured to express the bolus of liquid in response to positive pressure in a distal portion of the lumen created by movement of the elongate member distally in the lumen; and a wall defining a reservoir having a distal portion located proximate the chamber and being configured to provide liquid communication between the reservoir and the chamber and the reservoir includes a second elongate member slidably disposed therein and configured to displace the bolus from the reservoir to the chamber in response to movement of the second elongate member in the distal direction within the reservoir.

11. The catheter system of claim 10 wherein the elongate member and the second elongate member are coupled to one another for simultaneous sliding movement.

12. The catheter system of claim 10 wherein the bolus reservoir includes a distal inlet having a normally closed valve and second elongated member is retractable for operating the valve for charging the bolus reservoir with bolus.

13. A catheter system for delivering a bolus of liquid to a treatment site in a human body comprising:

a catheter having a proximal end, a distal end, and a lumen extending therein and formed of a material suitable for transluminally tracking through the vascular system to the treatment site, an extent of the catheter between the proximal and distal ends being profiled for transluminal advancement of the distal end of the catheter through a body lumen to a treatment site with the proximal end external to the body lumen for operation;

an elongate member, slidably disposed in the lumen, and having a distal end located proximate the distal end of the catheter; and a needle tip disposed at the distal end of the catheter, configured to express the bolus of liquid in response to positive pressure in a distal portion of the lumen created by movement of the elongate member distally in the lumen, the needle tip comprising a plurality of apertures spaced about an external periphery thereof.

14. The catheter system of claim 13 wherein the needle tip comprises: a porous needle tip.

\* \* \* \* \*